(12) United States Patent
Preisler

(10) Patent No.: US 11,998,649 B2
(45) Date of Patent: Jun. 4, 2024

(54) ANTIMICROBIAL, PUSH BUTTON SWITCH ASSEMBLY FOR USE AT A SELF-SERVICE, DISPENSING OR CHARGING STATION

(71) Applicant: JVIS-USA, LLC, Shelby Township, MI (US)

(72) Inventor: Darius J. Preisler, Macomb, MI (US)

(73) Assignee: JVIS-USA, LLC, Shelby Township, MI (US)

( * ) Notice: Subject to any disclaimer, the term of this patent is extended or adjusted under 35 U.S.C. 154(b) by 358 days.

(21) Appl. No.: 17/679,294

(22) Filed: Feb. 24, 2022

(65) Prior Publication Data

US 2023/0263919 A1    Aug. 24, 2023

(51) Int. Cl.
| | | |
|---|---|---|
| A61L 2/10 | (2006.01) | |
| B60L 53/30 | (2019.01) | |
| B67D 7/10 | (2010.01) | |
| B67D 7/86 | (2010.01) | |

(52) U.S. Cl.
CPC ............... *A61L 2/10* (2013.01); *B60L 53/30* (2019.02); *B67D 7/106* (2013.01); *B67D 7/86* (2013.01); *A61L 2202/11* (2013.01)

(58) Field of Classification Search
None
See application file for complete search history.

(56) References Cited

U.S. PATENT DOCUMENTS

| | | |
|---|---|---|
| 5,605,182 A | 2/1997 | Oberrecht et al. |
| 6,032,703 A | 3/2000 | Baker et al. |
| 6,157,871 A | 12/2000 | Terranova |
| 7,028,724 B2 | 4/2006 | Cohen et al. |
| 7,948,367 B1 | 5/2011 | Arauza |
| 7,948,376 B2 | 5/2011 | DeLine |
| 8,284,053 B2 | 10/2012 | DeLine |
| 8,747,143 B2 | 6/2014 | Ichio |
| 9,169,115 B2 | 10/2015 | Stefan et al. |
| 9,458,004 B2 | 10/2016 | Schulze |
| 10,014,615 B2 | 7/2018 | Mueller et al. |
| 11,360,258 B1 * | 6/2022 | Huwe .................. G02B 6/0068 |
| 2003/0041330 A1 | 2/2003 | Smith |
| 2004/0138924 A1 | 7/2004 | Pristine |
| 2004/0186744 A1 | 9/2004 | Lux |
| 2005/0261942 A1 | 11/2005 | Wheeler |
| 2006/0277071 A1 | 12/2006 | Shufeldt |
| 2007/0266010 A1 | 11/2007 | Sylthe et al. |

(Continued)

FOREIGN PATENT DOCUMENTS

WO    WO-2017178703 A1 *  10/2017  ............ A61J 1/2093

*Primary Examiner* — Andrew Smyth
(74) *Attorney, Agent, or Firm* — Brooks Kushman P.C.

(57) ABSTRACT

An antimicrobial, push button switch assembly for use at a self-service, dispensing or charging station is provided. The assembly includes a housing and a selection button supported for bi-directional movement within an opening in the housing. The selection button includes a plastic substrate and a plastic film sheet bonded to the substrate in a molding process. The film sheet has an outer touch surface configured to be pressed by a customer to initiate a dispensing or charging transaction. The film sheet is configured to allow at least one of germicidal light and antimicrobial agents to travel therethrough to the outer touch surface to disinfect the outer touch surface of pathogenic microorganisms.

19 Claims, 8 Drawing Sheets

(56) References Cited

U.S. PATENT DOCUMENTS

| | | |
|---|---|---|
| 2008/0040421 A1 | 2/2008 | VanKoevering |
| 2010/0128352 A1* | 5/2010 | Huang ................ G02B 6/0023 |
| | | 156/60 |
| 2014/0071073 A1 | 3/2014 | Williams et al. |
| 2015/0295344 A1 | 10/2015 | Sawada et al. |
| 2017/0101304 A1 | 4/2017 | Geipel et al. |
| 2018/0154029 A1* | 6/2018 | Shr .......................... A61L 2/10 |
| 2018/0339075 A1* | 11/2018 | Kennedy .................. A61L 2/24 |

* cited by examiner

ANTIMICROBIAL, PUSH BUTTON SWITCH ASSEMBLY FOR USE AT A SELF-SERVICE, DISPENSING OR CHARGING STATION

TECHNICAL FIELD

This application generally relates to antimicrobial, push button switch assemblies and, in particular, to such assemblies which are configured to be mounted and used at self-service dispensing or charging stations.

OVERVIEW

As described in U.S. patent document 2014/0071073 and with reference to FIG. 1, an exemplary fueling environment 10 may comprise a central building 12, a car wash 14, and a plurality of stations or islands 16 for refueling vehicles. The islands 16 may comprise fluid fueling islands such as liquid and gaseous hydrogen fueling islands. The islands may further include electric charging islands for recharging electric vehicles. The central building 12 need not be centrally located within the fueling environment 10, but rather is the focus of the fueling environment 10, and may house a convenience store 18 and/or a quick serve restaurant 20 therein. The convenience store 18, the quick serve restaurant 20 and the car wash 14 may include a point-of-sale (POS) device 22, 24, or 32, respectively. Each POS device 22, 24 or 32 may include a single computer or server operatively connected to an associated card reader and payment terminal. Additionally, each POS device 22, 24 or 32 may include a display, a touch screen, and/or other input devices.

The central building 12 may further house a site controller (SC) 26. The site controller 26 may control the authorization of fueling transactions and other conventional activities as is well understood, and the site controller 26 may preferably be in operative communication with each POS device. Alternatively, the site controller 26 may be incorporated at a POS device, such as the point of sale device 22, if needed or desired.

Further, the site controller 26 may have an off-site communication link 28 allowing communication with a remote host processing system 30 for credit/debit card authorization, content provision, reporting purposes or the like, as needed or desired. In one embodiment, the communication link 28 may be a stand alone router, switch, or gateway, although it should be appreciated that the site controller 26 may additionally perform the functions of, and therefore replace, such a device. The off-site communication link 28 may be routed through the Public Switched Telephone Network (PSTN), the Internet, both, or the like, as needed or desired. The remote host processing system 30 may comprise at least one server maintained by a third party, such as a financial institution. Although only one remote host processing system 30 is illustrated, those of skill in the art will appreciate that in a retail payment system allowing payment via payment devices issued by multiple payment card companies or financial institutions, the site controller 26 may be in communication with a plurality of remote host processing systems 30.

The fueling islands 16 may have one or more exemplary fuel dispensers 34 positioned thereon. The fuel dispensers 34 are in electronic communication with site controller 26 through any suitable link, such as two wire, RS 422, Ethernet, wireless, etc. if needed or desired.

FIG. 2 illustrates the fuel dispenser 34 that may operate in association with the site controller 26. The dispenser 34 typically includes a control system 42, which may be a processor, microprocessor, controller, microcontroller, or other suitable electronics with associated memory and software programs running thereon. The control system 42 is in operative communication with the site controller 26. The control system 42 further controls various aspects of the fuel dispenser 34 as described in more detail below.

In the illustrated embodiment, the dispenser 34 has a base 44 and a top 46, with a canopy 48 supported by two side panels 50. The fuel dispenser 34 is subdivided into multiple compartments. In this regard, a hydraulic area 52 encloses hydraulic components and an electronic area 54 encloses electronic components. A vapor barrier may be used to separate the hydraulic area 52 from the electronic area 54.

Fuel is pumped into an inlet pipe 56 in the hydraulic area 52. Fuel being dispensed passes through a meter 58. A displacement sensor 60 generates a signal in response to fuel flow signals indicative of the flow of fuel being dispensed are provide to the control system 42 via control data lines 62 which may provide control signaling to a valve 64 that may be open, partially open or closed to control the flow and blend of fuel therethrough.

As a dispensing transaction progresses, fuel is delivered to a hose 66 and through a nozzle 68 into the customer's vehicle. The dispenser 34 includes a nozzle boot 70, which may be used to hold and retain the nozzle 68 when not in use. The nozzle boot 70 may include a mechanical or electronic switch to indicate when the nozzle 68 has been removed for a fuel dispensing request and when the nozzle 68 has been replaced, signifying the end of a fueling transaction. A control line provides a signaling path from the electronic switch to the control system 42. The control system 42 may use signaling received via the control line in order to make a determination as to when a transaction has been initiated or completed.

Control/data lines 72 provide electronic communication between the control system 42 and a user interface 74. The user interface 74 includes various combinations of subsystems to facilitate customer interaction with the dispenser 34 and acceptance of payment of dispensed fuel. A bezel 76 acts as a lip around the various subsystems of the interface 74. In most cases, the bezel 76 is flush with the face of the fuel dispenser 34; however, in some embodiments it may extend outwardly from the face, in effect forming a raised lip. The bezel 76 may also comprise a plurality of sections that frame or house various subsystems or components.

As shown, the user interface 74 may include several input devices. For example, the user interface 74 may include a keypad 78. The keypad 78 is typically used for entry of a PIN if the customer is using a debit card for payment of fuel or other goods or services. User interface 74 may also include a card reader 80 for accepting credit, debit, or other chip or magnetic stripe cards for payment. Additionally, the card reader 80 may accept loyalty or program-specific cards.

The user interface 74 may also include other input devices such as a contactless card reader 82 (e.g. for integrated circuit or "smart" cards). Further, the user interface 74 may include other payment or transactional devices such as a bill acceptor 84, a receipt printer 86, and a change delivery device 88. The receipt printer 86 may provide a customer with a receipt of the transaction carried out at fuel dispenser 34. The change delivery device 88 may deliver change to a customer for overpayment. Other transactional devices, such as an optical reader and a biometric reader, are also contemplated.

A display 90 may be used to display information, such as transaction-related prompts and advertising, to the customer. In some embodiment, a touch screen may be used for the display 90. The customer may use soft keys 92 to respond to information requests presented to the user via the display 90. An intercom 94 may be provided to generate audible cues for the customer and to allow the customer to interact with an attendant. In addition, the dispenser 34 may include a transaction price total display 96 that presents the customer with the price for fuel that is dispensed. A transaction gallon total display 98 may be used to present the customer with the measurement of fuel dispensed in units of gallons or liters. Octane selection "buttons" 100 may be provided for the customer to select which grade or type of fuel is to be dispensed before dispensing is initiated. Finally, price per unit (PPU) displays 102 may be provided to show the price per unit of fuel dispensed in either gallons or liters, depending on the programming of the dispenser 34. When the customer selects one of the octane selection buttons 100, the control system 42 receives data identifying the selected octane and instructs the dispenser 34 to initiate dispensing of the selected fuel octane. Then, dispensing of the fuel may commence.

A grade select assembly and price per unit display may be utilized in the fuel dispenser 34 of FIG. 2. PPU displays 102 and octane selection buttons 100 may be incorporated into a grade select assembly (or selector). Since each dispenser 34 may have multiple grade selection options, the fuel dispenser 34 may include several separate grade select assemblies. Alternatively, several grade select assemblies may be integrated into a larger grade select panel. Grade select assemblies may be located at any appropriate location on the dispenser 34, such as below the display 90.

Each grade select assembly may be rectangular. However, it should be understood that one or more of the assemblies may take various shapes, such as triangular or circular. Also, in addition to octane selection button 100 and PPU display 102, each assembly may also include an indicator display.

A vehicle charging station, also called an EV charger or electric vehicle supply equipment (EVSE), is a piece of equipment that supplies electrical power for charging plug-in electric vehicles (including hybrids, neighborhood electric vehicles, trucks, buses, and others).

Although batteries can only be charged with DC power, many electric vehicles have onboard AC-to-DC converter that allows them to be plugged into a standard household AC electrical receptacle. Inexpensive lower-power public charging stations will also provide AC power, known as "AC charging stations." To facilitate higher power charging, which requires much larger AC-to-DC converters, the converter may be built into the charging station instead of the vehicle, and the station supplies already-converted DC power directly to the vehicle, bypassing the vehicle's onboard converter. These are known as "DC charging stations." Many fully electric car models can accept both AC and DC power.

Charging stations provide connectors that conform to a variety of standards. DC charging stations are commonly equipped with multiple connectors to be able to supply a wide variety of vehicles. Public charging stations are typically found street-side or at retail shopping centers, government facilities, and other parking areas.

U.S. Pat. No. 8,747,143; 2015/0295344; and U.S. Pat. No. 10,014,615 show a variety of charging connector assemblies.

Fuel dispensers are used to pump gasoline, diesel, compressed natural gas, $CGH_2$, HCNG, LPG, gaseous hydrogen, kerosene, alcohol fuel (like methanol, ethanol, butanol, propanol), biofuels (like straight vegetable oil, biodiesel), or other types of fuel into the tanks within vehicles and calculate the financial cost of the fuel transferred to the vehicle. Besides fuel dispensers, one other significant device which is also found in filling stations and can refuel certain (compressed-air) vehicles is an air compressor, although generally these are just to inflate car tires.

The convenience stores found in filling stations typically sell confections, alcoholic beverages, tobacco products, lottery tickets, soft drinks, snacks, coffee, newspapers, magazines, and, in some cases, a small selection of grocery items, such as milk. Some also sell propane or butane and have added shops to their primary business. Conversely, some chain stores, such as supermarkets, discount stores, warehouse clubs, or traditional convenience stores, have provided fuel pumps on their premises.

In most stations in Canada and the US, the pump has a single nozzle and the customer selects the desired octane grade by pushing a button. Some pumps require the customer to pick up the nozzle first, then lift a lever underneath it; others are designed so that lifting the nozzle automatically releases a switch. Some newer stations have separate nozzles for different types of fuel. Where diesel fuel is provided, it is usually dispensed from a separate nozzle even if the various grades of gasoline share the same nozzle.

Fuel pumps and charging connectors are only a few examples of items in the general public with surfaces that are contacted by an inordinate amount of people that can harbor pathogens highly associated with illness and disease. *E-coli*, salmonella and staphylococcus-aureus are examples of types of bacteria that can be found on commonly-used surfaces that can be easily spread to those in the general public through contact with these surfaces. If untreated, these types of bacteria can have adverse effects on one's well being such as serious illness and possibly death.

U.S. Pat. Nos. 7,028,724; 7,948,376; 9,458,004; 2017/0101304; and 10,994,040 show a variety of filling stations and nozzles associated therewith. In particular, U.S. Pat. No. 10,994,040 discloses a disinfection illuminator having ultraviolet radiation sources which can irradiate a number of contact surfaces. A control unit can control the ultraviolet irradiation of the contact surfaces. The disinfection illuminator is suitable for a wide variety of devices that are used by the general public. Gas station pumps, door knobs, key pads, and bathrooms are illustrative of examples of some devices and places having commonly-used surfaces that can be treated by the disinfection illuminator.

U.S. Pat. No. 7,948,376 discloses a fuel dispenser including a nozzle containing an antimicrobial coating. A camera generates images to detect the nozzle and captures images of the user to track the user and to determine the identity of the user. The nozzle may include a fueling button that illuminates red or green. The nozzle may include an RFID reader. The dispenser may include a tag or transponder reader.

Automated teller machines (ATMs); self-service, fuel dispensing stations; self-service, electric charging stations; and dispensing kiosks are typical examples of self-service technologies. A kiosk is a small self-standing physical structure (often including a computer and a display screen) that displays information for people walking by. More sophisticated kiosks let users interact and include touch screens, keyboards, sound, and motion video. Examples of kiosk systems are disclosed in the following U.S. patent documents: 2004/0138924; 2004/0186744; 2005/0261942; 2006/277071; 2007/0266010; and 2008/0040421.

Facial recognition is a technology capable of matching a human face from a digital image or a video frame against a database of faces, typically employed to authenticate users through ID verification services. The technology works by pinpointing and measuring facial features from a given image.

Computerized facial recognition involves the measurement of a human's physiological characteristics. Facial recognition is a type of biometrics. Facial recognition systems have been deployed in advanced, human-computer interaction, video surveillance and automatic indexing of images.

U.S. Pat. No. 8,284,053 discloses a fuel dispenser comprising fuel dispensing apparatus mounted within a housing and a nozzle for dispensing fuel. The fuel dispensing apparatus includes control electronics and at least one touch display mounted in the housing and operatively coupled to the control electronics. The touch display is configured to allow a user to make selections for conducting a transaction. A camera or other suitable proximity detector is configured to detect the presence of a user and whether the user exceeds a height threshold without the user physically touching the fuel dispenser. In response to detecting the presence of the user, the fuel dispenser control electronics activates the display so that instructions are presented to the user in a first orientation or a second orientation depending on whether the user's height exceeds the threshold.

U. S. patent document 2003/0041330 discloses a related security camera system in a fuel dispenser.

U.S. Pat. No. 7,948,367 discloses a fuel dispenser comprising a housing, a fuel dispensing apparatus mounted within the housing, control electronics operatively connected to the fuel dispensing apparatus, at least one display mounted in the housing and operatively coupled to the control electronics, and a nozzle operatively coupled to the fuel dispensing apparatus and the fuel dispensing apparatus control electronics, the nozzle configured to produce electromagnetic signals. The dispenser is configured to trigger an alarm when the nozzle is brought into close proximity to the at least one display to prevent the user from using the nozzle to make data entries.

As described in U.S. Pat. No. 6,032,703 (i.e. '703 patent), as governmental regulations pertaining to automotive exhaust emissions become ever more stringent, it is becoming necessary to provide fuels which are adapted to a particular vehicle being refueled. For example, it may be necessary to provide more highly oxygenated fuels to certain vehicles. With diesel engines, and other types of engines, it may be necessary to provide enriched fuels or auxiliary fluids such as water-borne urea additives which would, for example, be placed in a separate tank of a vehicle, so as to be available for an aftertreatment process within a vehicle's catalytic control system.

Another factor affecting fueling in the future will be the use of fuel cells which cannot operate with fuel additives such as detergents and anti-wear additives for fuel pump protection which are necessary for diesel and gasoline engines.

As a result of the varying fuel needs presented by future model vehicles, it would likely be necessary to burden the fuel infrastructure with the need to distribute many different types of blended fuels. A system is desired to avoid the need for distributing various types of blended fuels by providing a base fuel and an additive system.

Another problem with requiring different types of fuels is that improper fueling becomes a possibility. It may be difficult for future consumers to know and specify exactly what fuel is needed for a vehicle.

Finally, in the event that an automotive emission control system has adaptable controls so that, for example, a change in the efficiency of the control system may be corrected through the use of a fuel having a specific additive, it is desirable to be able to communicate this change in the fueling need of the vehicle to the fueling station.

The Mobil Oil Corporation currently has an electronic transponder device which communicates with a fuel pump so as to identify the holder of a fuel or other type of credit card.

The '703 patent discloses a system for fueling an automotive vehicle which includes a transmitter mounted on the vehicle for identifying the type of fuel required by the vehicle and a fuel control and communication subsystem providing fuel which is blended to achieve the characteristics called for by the vehicle mounted transmitter.

U.S. Pat. No. 5,605,182 discloses a vehicle identification system for a fuel dispenser.

As described in U.S. Pat. No. 9,169,115 (i.e. '115 patent), with rising oil prices, gas stations are increasingly subjected to cases of fuel theft. The magnitude of the theft in many countries is quite large and accounts for sizeable monetary losses for the gas stations. In order to counter the problem of fuel theft, gas stations maybe fitted with monitoring cameras that record the auto license plate of each vehicle being refueled in order to enable the detection of the respective offender in the event of a theft. This is, however, costly on the one hand and on the other hand (e.g. in cases of the use of false license plates or stolen vehicles) provides no guarantee that the gas station operator will actually be compensated. Specifically, it may be costly to track down the thief using the license plate as an identifier. Legal fees associated with criminal prosecution of the thieves may also be costly. It will be appreciated that theft has also been anticipated in vehicles using other types of fuel (e.g., diesel, ethanol, hydrogen, etc.) or forms of energy such as electricity.

The '115 patent discloses a method for preventing fuel theft at a gas station or a charging station for motor vehicles. The method includes determining whether a refueling process or recharging process of a motor vehicle is taking place and activating an emergency operating mode of the motor vehicle until a payment for the refueling process or the recharging process has taken place, the emergency operating mode configured to limit vehicle speed.

U.S. Pat. No. 6,157,871 discloses a fuel dispensing system comprising a fuel dispenser associated with a control system adapted to detect a drive-off when fuel is delivered and not paid for, and generate a drive-off signal when a drive-off condition is detected. A receiver is associated with the control system and adapted to receive signals including identification indicia from a remote communications unit associated with the customer. A transmitter associated with the control system is adapted to transmit the drive-off signal to the remote communications unit. The drive-off signal is adapted to cause the remote communications unit to take measures to prevent future transactions involving that customer, and, in particular, the remote communications unit.

Methods and systems which help detect and prevent crime at a gas station or a charging station can aid law enforcement in capturing perpetrators of attempted theft. In fact, the mere presence of such systems at a gas station or charting station can act as a powerful deterrent against would-be criminals.

Present approaches of treating commonly-used surfaces to prevent the spreading of microbial diseases typically include applying chemical disinfectants to the surfaces. While these chemical disinfectants can be effective at eradicating harmful bacteria, it is still difficult to effectively prevent the alarming rate in which the bacteria spreads within the general public. In addition, these chemical disinfectants can be harmful to the health of those that apply the chemicals to the commonly-used surfaces.

Coronavirus disease 2019 (COVID-19) was first reported in December 2019 and then characterized as a pandemic by the World Health Organization on Mar. 11, 2020. Despite extensive efforts to contain the spread of the disease, it has spread worldwide with over 5.3 million confirmed cases and over 340,000 confirmed deaths as of May 25, 2020. Transmission of SARS-CoV-2, the beta coronavirus causing COVID-19, is believed to be both through direct contact and airborne routes, and studies of SARS-CoV-2 stability have shown viability in aerosols for at least 3 hours. Given the rapid spread of the disease, including through asymptomatic carriers, it is of clear importance to explore practical mitigation technologies that can inactivate the airborne virus in public locations and thus limit airborne transmission.

To maintain an active infectious disease in a human population, a pathogen must be transmitted from one host or source to another. Transmission occurs by four main routes: airborne, contact, vehicle, and vector-borne.

Airborne Transmission

Because air is not a suitable medium for the growth of a pathogen, any pathogen that is airborne must have originated from a source such as humans, other animals, plants, soil, food, or water. In airborne transmission the pathogen is suspended in the air and travels over a meter or more from the source to the host. The pathogen can be contained within droplet nuclei or dust. Droplet nuclei are small particles, 1 to 4 μm in diameter, that result from the evaporation of larger particles (10 μm or more in diameter) called droplets. Droplet nuclei can remain airborne for hours or days and travel long distances.

When animals or humans are the source of the airborne pathogen, it usually is propelled from the respiratory tract into the air by an individual's coughing, sneezing, or vocalization.

Aerosols and droplets generated during speech have been implicated in the person-to-person transmission of viruses, and there is current interest in understanding the mechanisms responsible for the spread of Covid-19 by these means. The act of speaking generates oral fluid droplets that vary widely in size, and these droplets can harbor infectious virus particles. Whereas large droplets fall quickly to the ground, small droplets can dehydrate and linger as "droplet nuclei" in the air, where they behave like an aerosol and thereby expand the spatial extent of emitted infectious particles.

The table immediately below summarizes some human airborne pathogens and the diseases they cause in humans.

| Microorganism | Disease |
| --- | --- |
| Viruses | |
| Varicella | Chickenpox |
| Influenza | Flu |
| Rubeola | Measles |
| Rubella | German measles |
| Mumps | Mumps |
| Poliomyelitis | Polio |
| Acute respiratory viruses | Viral pneumonia |
| Pulmonary syndrome hantavirus | Hantavirus pulmonary syndrome |
| Bacteria | |
| *Actinomyces* spp. | Lung infections |
| *Bordetella pertussis* | Whooping cough |
| *Chlamydia psittaci* | Psittacosis |
| *Corynebacterium diphtheriae* | Diphtheria |
| *Mycoplasma pneumoniae* | Pneumonia |
| *Mycobacterium tuberculosis* | Tuberculosis |
| Neisseria meningitidis | Meningitis |
| *Streptococcus* spp. | Pneumonia, sore throat |
| Fungi | |
| *Blastomyces* spp. | Lung infections |
| *Coccidioides* spp. | Coccidioidomycosis |
| *Histoplasma capsulatum* | Histoplasmosis |

A study conducted by Asahi Kasei and Nara Medical University confirmed that 226 nm UV-C LEDs are able to quickly inactivate coronavirus (SARS-CoV-2) while having significantly less effect on animal skin cells than 270 nm UV-C LEDs.

The inactivation (killing) of viruses and other pathogens using UV light rather than chemical disinfectants has drawn greater attention with the COVID-19 pandemic. Nevertheless, it has been necessary to prevent light from conventional mercury UV lamps (254 nm) and UV-C LEDs (260-280 nm) from directly irradiating human skin due to risk of harmful effects.

In contrast, UV excimer lamps have a wavelength of 222 nm showed negligible effect on the human body. However, LEDs are more compact and allow greater flexibility in design, have less risk of breaking, and have a quicker startup time than traditional lamps, opening up new potential for smaller, safer, and more responsive applications of UV-C light.

Crystal IS, an Asahi Kasei Company, has commercialized Klaran UV-C LEDs in the 260-270 nm wavelength range, and is now supporting the advanced research by Asahi Kasei to reach shorter wavelengths. Recently, Asahi Kasei's Corporate Research & Development was able to create 226 nm UV-C LED prototypes, and tests were conducted for these LEDs regarding their efficacy for inactivating SARS-CoV-2 as well as their effects on animal skin cells.

All of the UV-C LEDs used in the above-noted study were created form the proprietary aluminum nitride (AIN) substrate and pseudomorphic aluminum gallium nitride (AlGaN) technology of Crystal IS.

SUMMARY OF EXAMPLE EMBODIMENTS

An object of at least one embodiment of the present invention is to provide an antimicrobial, push button switch assembly for use at a self-service dispensing or charging station wherein a plastic film sheet of a selection button is configured to allow at least one of antimicrobial agents and germicidal light to travel therethrough to an outer touch surface of the film sheet to disinfect the outer touch surface of pathogenic microorganisms.

In carrying out the above object and other objects of at least one embodiment of the present invention, an antimicrobial, push button switch assembly for use at a self-service, dispensing or charging station is provided. The assembly includes a housing and a selection button supported for bi-directional movement within an opening in the housing. The selection button includes a plastic substrate and a plastic film sheet bonded to the substrate in a molding process. The film sheet has an outer touch surface configured to be pressed by a customer to initiate a dispensing or charging transaction. The film sheet is configured to allow at least one of germicidal light and antimicrobial agents to travel therethrough to the outer touch surface to disinfect the outer touch surface of pathogenic microorganisms.

The film sheet may comprise a UV light transmissive waveguide.

The film sheet may include a clear plastic surface layer which has the antimicrobial agents which exhibit controlled migration through the surface layer to the outer touch surface.

The film sheet may include a clear plastic surface layer which may comprise a UV light transmissive waveguide.

The assembly may further comprise a UV light source optically coupled to the waveguide and configured to emit germicidal light into the waveguide so that the UV light travels through the waveguide to the outer touch surface.

The switch assembly may have a normally open state and a temporary closed state to electrically close a normally open control circuit or controller when the touch surface is pressed.

The molding process may be an injection molding process during which plastic of the substrate is injected into a mold cavity wherein temperature and pressure within the mold cavity is sufficient to melt a bottom surface of the film sheet during the injection molding process to bond the substrate to the film sheet and wherein the mold cavity has a shape defining the selection button.

The germicidal light may be UV light which has an intensity within a relatively narrow range of wavelengths which kills microbes without damaging healthy tissue of the customer.

The UV light may be a far UV-C light having a wavelength range of about 200 nm to about 230 nm.

The assembly may further comprise an illumination device to illuminate at least one of the selection button and the area proximate the selection button.

The illumination device may include an array of visible light LEDs.

The UV light source may include an array of UV light LEDs.

The film sheet may be a pre-painted film sheet which provides information to the customer.

The film sheet may include a clear plastic layer which may comprise an acrylic polymer clear coat layer.

The plastic substrate may be molded from a thermoplastic resin and has an outer surface.

The plastic film sheet may have a membrane bonded to the outer surface of the substrate.

The plastic film sheet may include a layer of acrylic color bonded to the membrane and separate from the substrate.

The plastic film sheet may include a layer of polyvinylidene fluoride overlying and protecting the layer of acrylic color.

DETAILED DESCRIPTION

Figure 1:
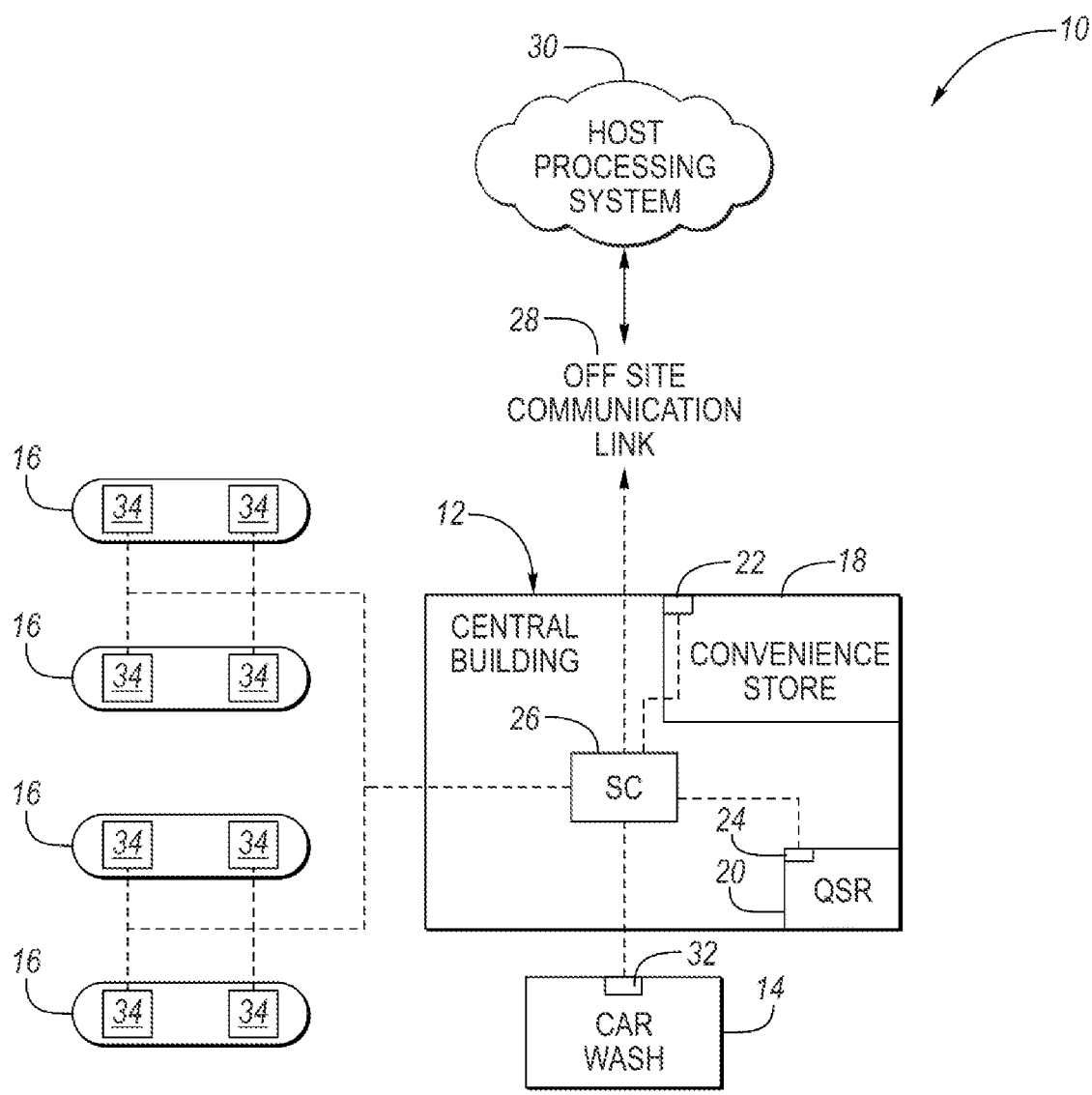
FIG. 1 is a diagrammatic representation of a retail fuel dispensing environment in which an embodiment of the present invention may be utilized.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

"Antimicrobial" is equivalent to antibacterial, antifungal, antiviral, antiparasitic, microbicidal, and microbistatic. Most antimicrobial agents control microorganism growth by penetrating the microorganism's thin cellular walls, thereby interrupting the organism's metabolic function, and finally killing said organism.

A part having "antimicrobial properties" or characteristics includes any material that kills or inhibits growth of a microorganism.

A "microorganism" corresponds to bacteria, fungi, archea and protists and, most typically, the microorganism is unicellular.

"Dispersed throughout" corresponds to the dispersal of a species, e.g., an antimicrobial additive or agent, homogeneously or heterogeneously throughout a plastic layer which may be clear. For example, the antimicrobial agent may be homogeneously dispersed throughout a surface layer such that the concentration of antimicrobial agent at its surface is substantially the same as the concentration at any other sampling location in the layer. Heterogeneous dispersal corresponds to more antimicrobial agent at one sampling location in the layer relative to some other sampling location in the layer. For example, there may be more antimicrobial agent at the surface relative to other sampling locations or there may be islands of more concentrated antimicrobial agent throughout the layer.

As used in this application, the term "substrate" refers to any flexible, semi-flexible or rigid single or multi-layer component having a surface to which a decorative, UV-light transmissible or transparent membrane or film is or can be applied. The substrate may be made of polymers and other plastics, as well as composite materials. Furthermore, the size and shape of the substrate and, particularly, the surface to be covered can be any part of an assembly or device manufactured by any of various methods, such as, without limitation, conventional molding, deep-drawing, extruding, or otherwise fabricated.

The term "overlies" and cognate terms such as "overlying" and the like, when referring to the relationship of one or a first, superjacent layer relative to another or a second, subjacent layer, means that the first layer partially or completely lies over the second layer. The first, superjacent layer overlying the second, subjacent layer may or may not be in contact with the subjacent layer; one or more additional layers may be positioned between respective first and second, or superjacent and subjacent layers.

As used herein, a material/structure is considered to be "reflective" to ultraviolet light of a particular wavelength when the material/structure has an ultraviolet reflection coefficient of at least 30 percent for the ultraviolet light of the particular wavelength. A highly ultraviolet reflective material/structure has an ultraviolet reflection coefficient of at least 80 percent.

A material, structure or layer is considered to be "transparent" to ultraviolet radiation of a particular wavelength when the material/structure/layer allows at least ten percent of radiation having a target wavelength, which is radiated at a normal incidence to an interface of the material/structure/layer to pass therethrough.

Figure 2:
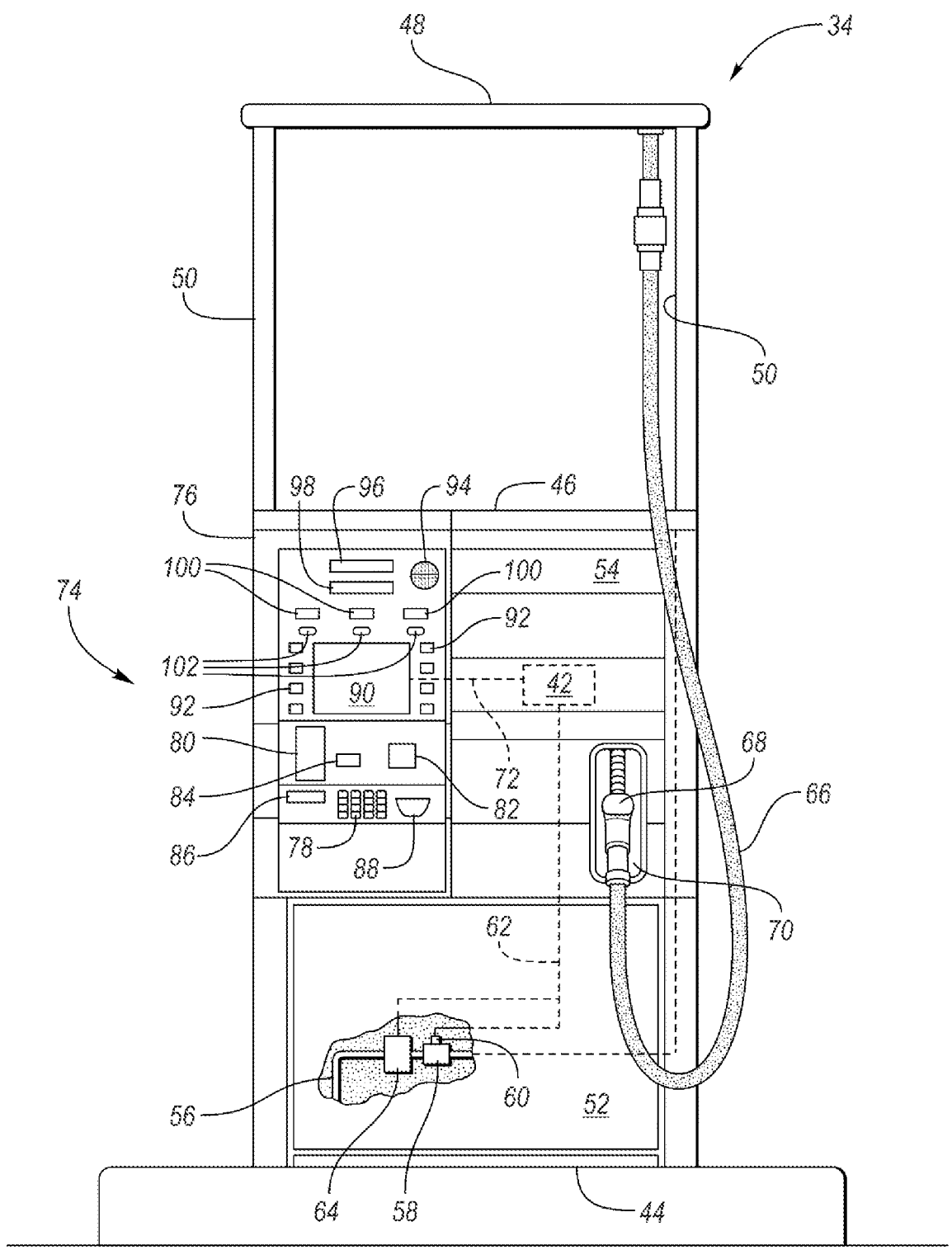
FIG. 2 is a front elevational view, partially broken away, of a prior art fuel dispenser within the retail fueling environment of FIG. 1 that incorporates a grade select assembly.
Figure 3:
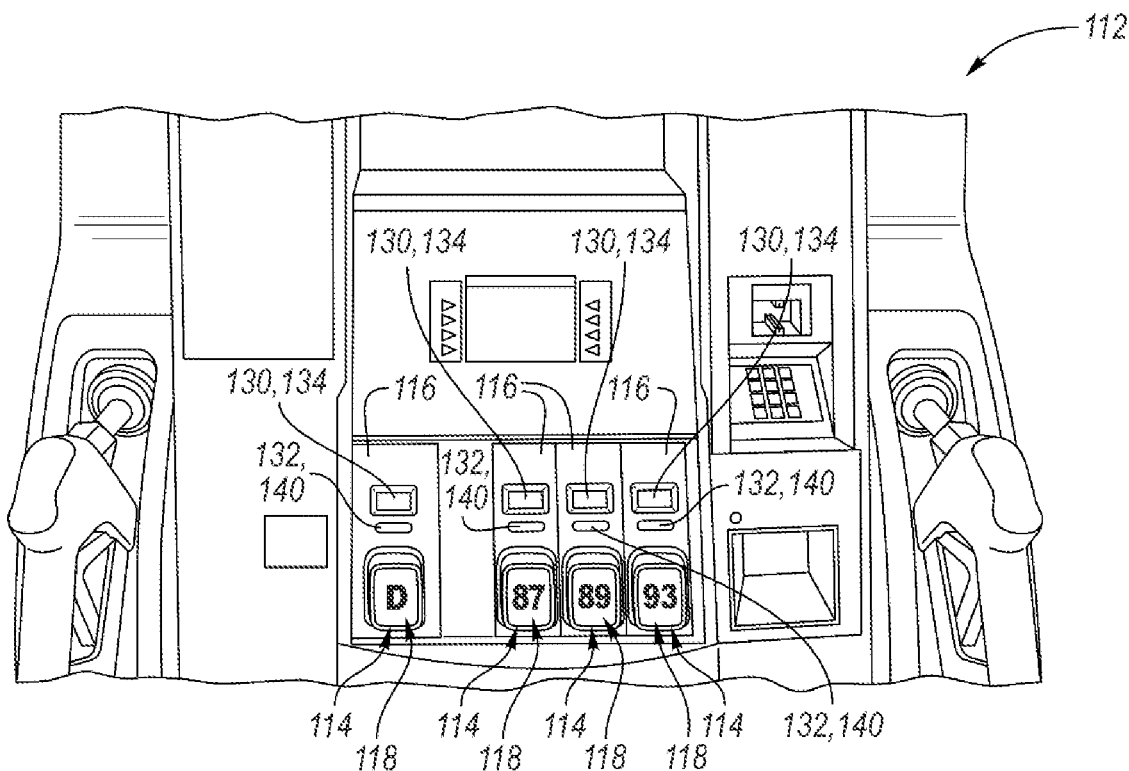
FIG. 3 is a front elevational view, partially broken away, of a fuel dispenser capable of dispensing multiple fuels and fuel blends.
Figure 4:
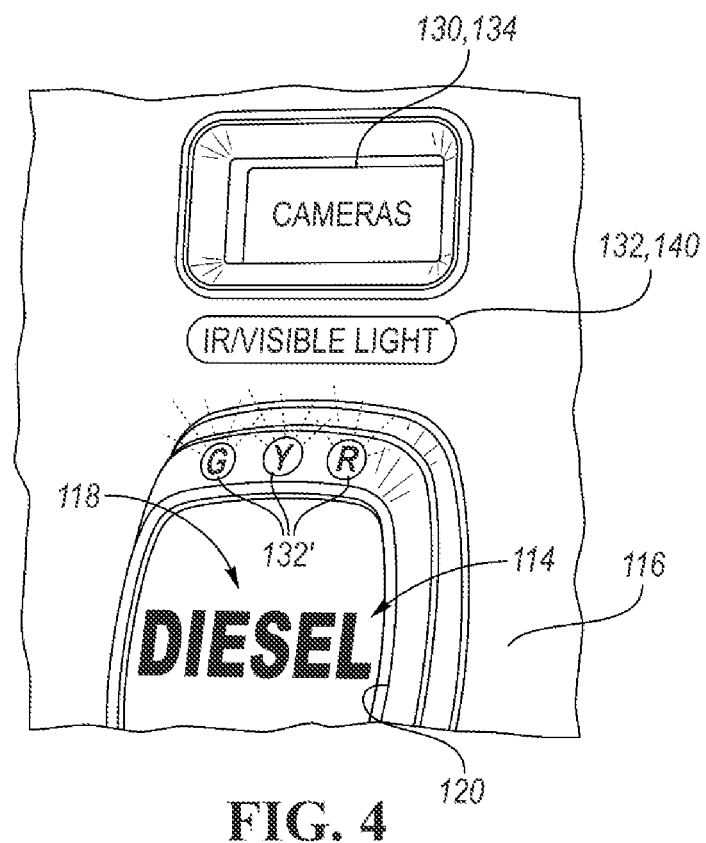
FIG. 4 is an enlarged front perspective view, partially broken away, of a fuel select assembly that may be utilized with the fuel dispenser of FIG. 3.
Figure 5:
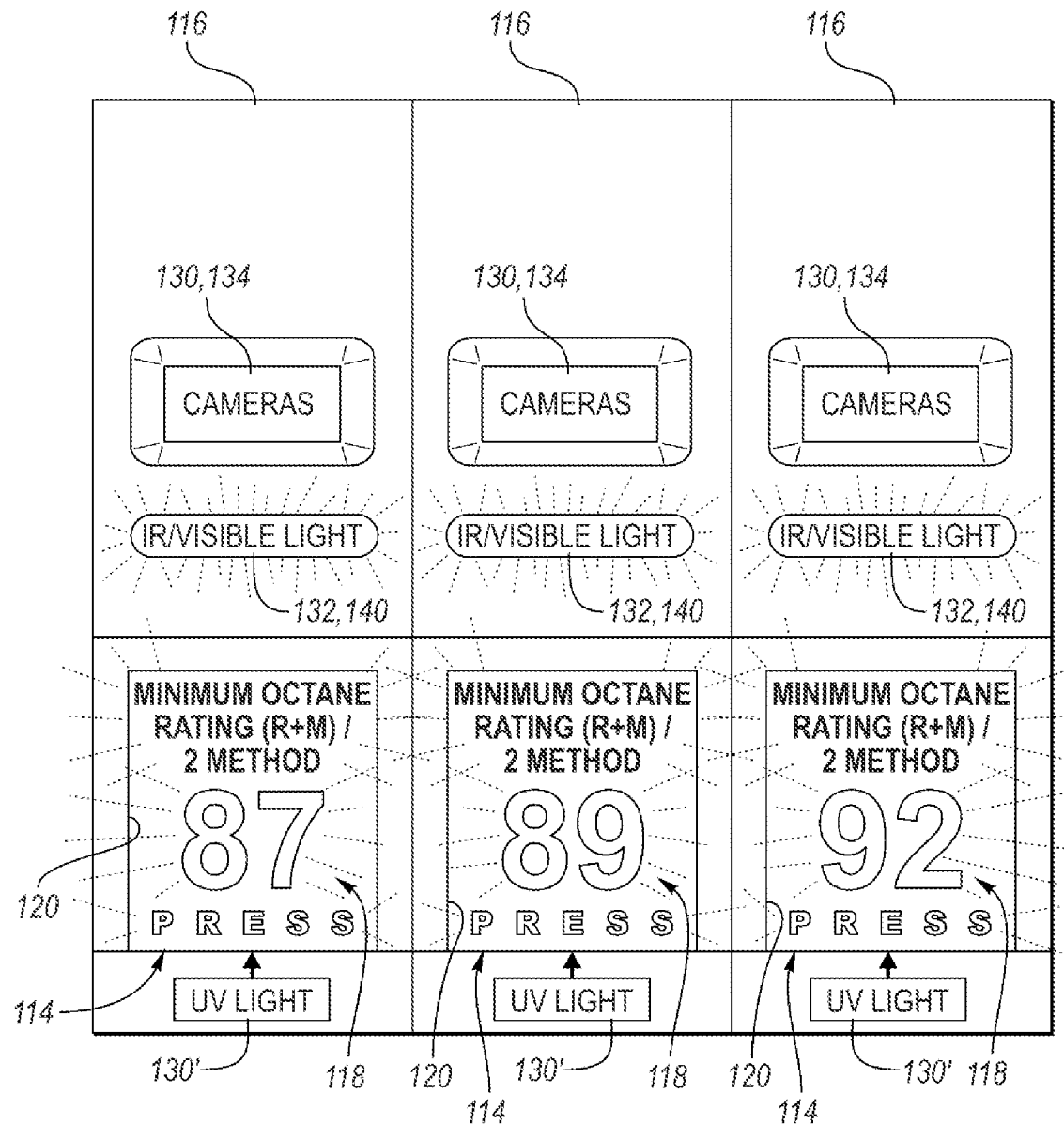
FIG. 5 is an enlarged front view of a grade select assembly that may be utilized with the fuel dispenser of FIG. 3.
Figure 9:
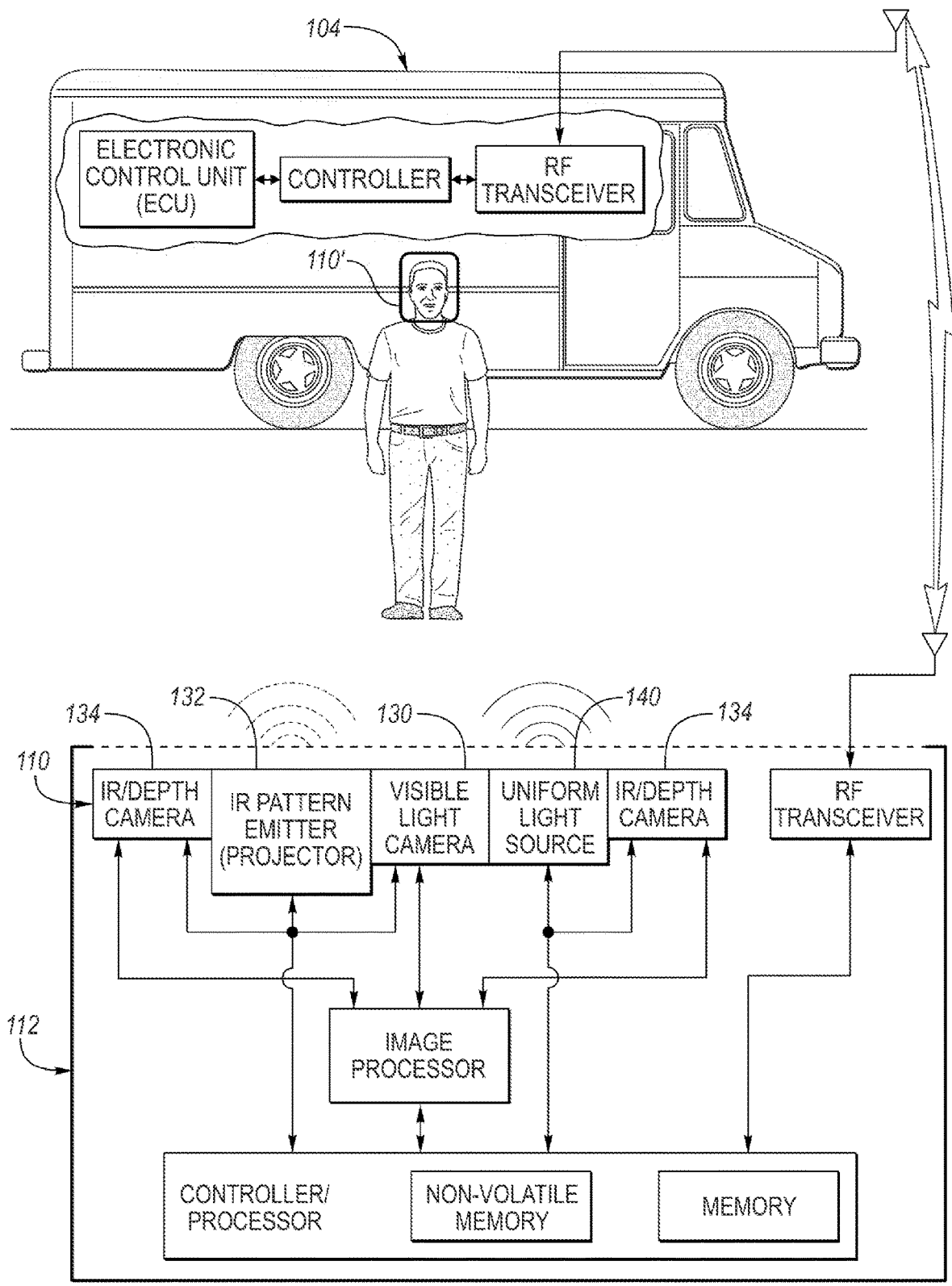
FIG. 9 is a combined schematic and block diagram view, partially broken away, including a mobile communication device supported on a vehicle; a human is standing between the vehicle and an apertured housing of a fuel dispenser; a stationary communication device is supported on the fuel dispenser; the block diagram also includes a 3D or depth sensor, an image processor and a controller/processer.

Referring again to the drawing Figures, FIG. 9 illustrates a vehicle, generally indicated at 104. The vehicle 104 is illustrative of any type of automobile or other vehicle. For example, the vehicle 104 may include, but is not limited to, cars, trucks, SUVs, semi-trucks, tractors, boats, etc. The vehicle 104 is located at a self-service fuel dispensing or charging station generally of the type illustrated in FIGS. 1-3 for refueling or recharging, respectively. A human is shown between the vehicle 104 and a fuel dispenser, generally indicated at 112.

The fuel dispenser 112 includes at least one antimicrobial, push button switch assembly, generally indicated at 114 in FIGS. 3-5 and 10, for use at the self-service dispensing or charging station. Each assembly 114 includes a housing or enclosure 116 and a selection button, generally indicated 118, supported for bi-directional movement within an opening 120 in the housing 116. The housing or enclosure 116 may be made of a thermoplastic resin, TPO, ABS, PC/ABS, or polypropylene with a mold-in color.

Figure 6:
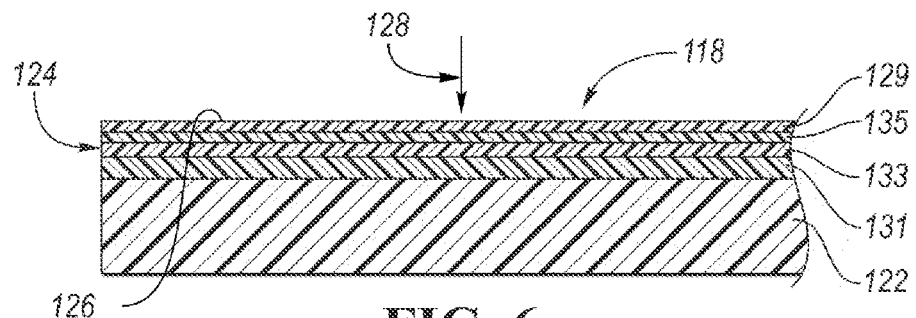
FIG. 6 is an enlarged view, partially broken away and in cross section, of a top portion of a selection button that may be utilized with the assemblies of FIGS. 3, 4 and 5.
Figure 8:
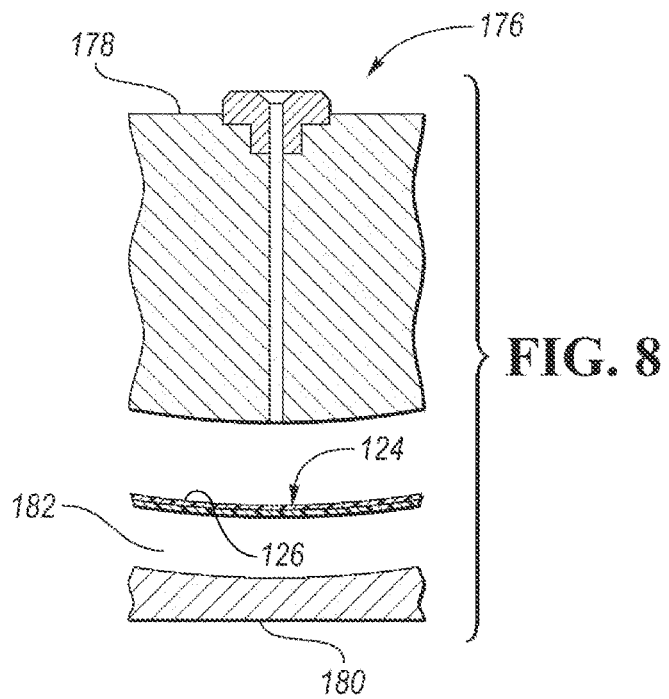
FIG. 8 is a schematic view, partially broken away and in cross section, of a conventional injection molding system which may be utilized to make plastic selection buttons; a mold of the system is depicted in its open position with a formed plastic film sheet placed between two mold halves of the system.

Referring to FIG. 6, the button 118 includes a plastic substrate 122 and a plastic film sheet, generally indicated at 124, bonded to the substrate 122 in a molding process as illustrated in FIG. 8. The film sheet 124 has an outer touch surface 126 configured to be pressed as indicated by arrow 128 by a customer to initiate a dispensing or charging transaction. The film sheet 124 is configured to allow antimicrobial agents to travel therethrough to the outer touch surface 126 to disinfect the outer touch surface 126 of pathogenic microorganisms. The film sheet 124 includes a clear plastic surface layer 129 which has the antimicrobial agents which exhibit controlled migration through the surface layer 129 to the outer touch surface 126.

The film sheet 124 may be a thin membrane composite having a thickness of less than 0.5 millimeters. The film sheet 124 is preferably pre-painted. The film sheet 124 is preferably a polyester sheet such as Mylar®, a polyurethane or polycarbonate sheet.

The substrate 122 may be formed from a thermoplastic resin such a polyolefin, polycarbonate, tee tpe, sebs tpe, and a mixture of polycarbonate and acrylonitrile/butadiene/styrene (ABS). The corresponding film layer or sheet 124 is compatible with the plastic of the substrate 122 so that diffusion between contact surfaces occurs in the molding method described.

The film sheet 124 preferably has the following coatings placed on a membrane 131, a layer 133 of acrylic color in mating contact with the membrane 131 and a layer 135 of polyvinylidene fluoride (PVDF) with the acrylic clear coat or surface layer 129 to protect the film from damage and to provide film elasticity, chemical resistance, stain resistance, weathering and UV protection. In a preferred embodiment, the PVDF layer comprises most of the total pre-form thickness which is less than 1.0 mils and is preferably about 0.2 mils.

Referring again to FIG. 8, there is illustrated a conventional injection mold, generally indicated at 176, of a system (not shown) for making the plastic selection button 118. With such a system there is included an injection molding machine (not shown) having a nozzle (not shown) for injecting predetermined amounts of shots of molten resin. The injection molding machine includes a hydraulic screw ram (not shown) which is disposed in a bore formed in a barrel (not shown) of the injection molding machine. The ram plasticizes and advances resin towards the nozzle. Upon complete plasticization of the resin, the screw ram is hydraulically advanced towards threaded portions of the barrel to inject molten plastic through the nozzle, as is well known in the art.

As depicted in FIG. 8, opposing surfaces of mold parts 178 and 180, respectively, of the mold 176 define a mold cavity 182 with the formed film sheet 124 disposed therein. FIG. 8 illustrates an open position of the mold 176.

The one-piece film sheet 124 is first placed in the mold cavity 182 in the open position of the mold 176. Thereafter, the substrate 122 is molded in the mold 176 of the plastic injection molding system to form the completed unitary, laminate, plastic selection button 118.

In an alternative embodiment, the mold 176 can be modified to produce a plastic button with embossed lettering. This embossed effect is achieved by etching into the mold 176 the desired pattern or letters so that the letters have at least a 0.5 millimeter radius on the edge of the letter, or else the film sheet 124 may tear and stretch.

The unique features of the laminate selection button 118 are: 1) a stiff inner material (i.e. substrate 122) to support the intended application; 2) reduction and/or elimination of paint problems such as drips, runs, spits, dry spray, light coverage and gloss and improved color match and paint adhesion; 3) reduced molding scrap due to splay, flow marks and minor surface imperfections (in the substrate 122), which can be completely covered by the film sheet 124; and 4) increased durability of the resulting plastic laminate selection button 118.

Prior to injection molding, the painted film sheet 124 may be placed in a vacuum mold (not shown) which is operated to form a pre-form if the film sheet 124 is to have anything other than a planar shape.

Molten plastic is injected into the mold 176 through its injection aperture at a temperature and pressure sufficient to melt the bottom surface layer of the film sheet 124 or pre-form. Then the selection button 118 is cooled to a temperature beneath the softening point of both resins.

As described above, the molding process is an injection molding process during which plastic of the substrate 122 is injected into the mold cavity 182 wherein temperature and pressure within the mold cavity 182 is sufficient to melt a bottom surface of the film sheet 124 during the injection molding process to bond the substrate 122 to the film sheet 124 and wherein the mold cavity 182 has a shape defining the selection button 118.

The film sheet 124 may be a pre-painted film sheet which provides information such as fuel grade or type to the customer.

The film sheet 124 may include the clear plastic layer 129 which may comprise an acrylic polymer clear coat layer. The plastic substrate 122 may be molded from a thermoplastic resin. The plastic film sheet 124 may have the lower surface of the membrane 131 bonded to the outer upper surface of the substrate 122. The plastic film sheet 124 may include the layer 133 of acrylic color bonded to the membrane and separate from the substrate 122. The plastic film sheet 124 may include the layer 135 of polyvinylidene fluoride overlying and protecting the layer 133 of acrylic color.

The antimicrobial additive or agent within the surface layer 129 may comprise an antimicrobial substance, which is non-toxic and free of heavy metal and may be a chlorinated phenol (e.g., 5-chloro-2-(2, 4-dichlorophenoxy) phenol). An alternative antimicrobial agent is polyhexamethylene biguanide hydrochloride (PHMB). Other chemical compounds having known antimicrobial characteristics may also be used. The preferred method is to incorporate the antimicrobial additive or agent into a synthetic, polymeric master batch prior to film sheet formation.

Figure 7:
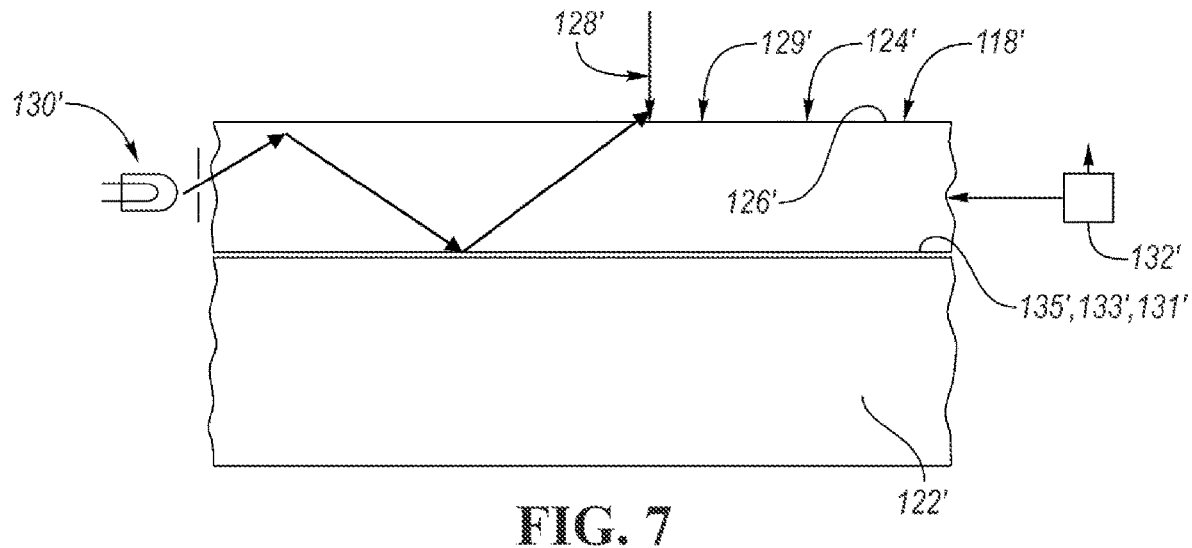
FIG. 7 is a conceptual diagram illustrating a portion of the selection button of FIG. 6 together with typical UV and visible light sources.

Referring now to FIG. 7, a second embodiment of a switch assembly, generally indicated at 114', includes a selection button 118' having a film sheet 124' (greatly enlarged for illustrative purposes) which does not include antimicrobial agents but rather is configured to allow germicidal light from a UV light source 130' to travel therethrough to an outer touch surface 126' to disinfect the outer touch surface 126' of pathogenic microorganisms. The button 118' also includes layers 135', 133', 131', 129' and 122' substantially the same as the layers 135, 133, 131, 129 and 122, respectively, of the first embodiment.

Figure 11:
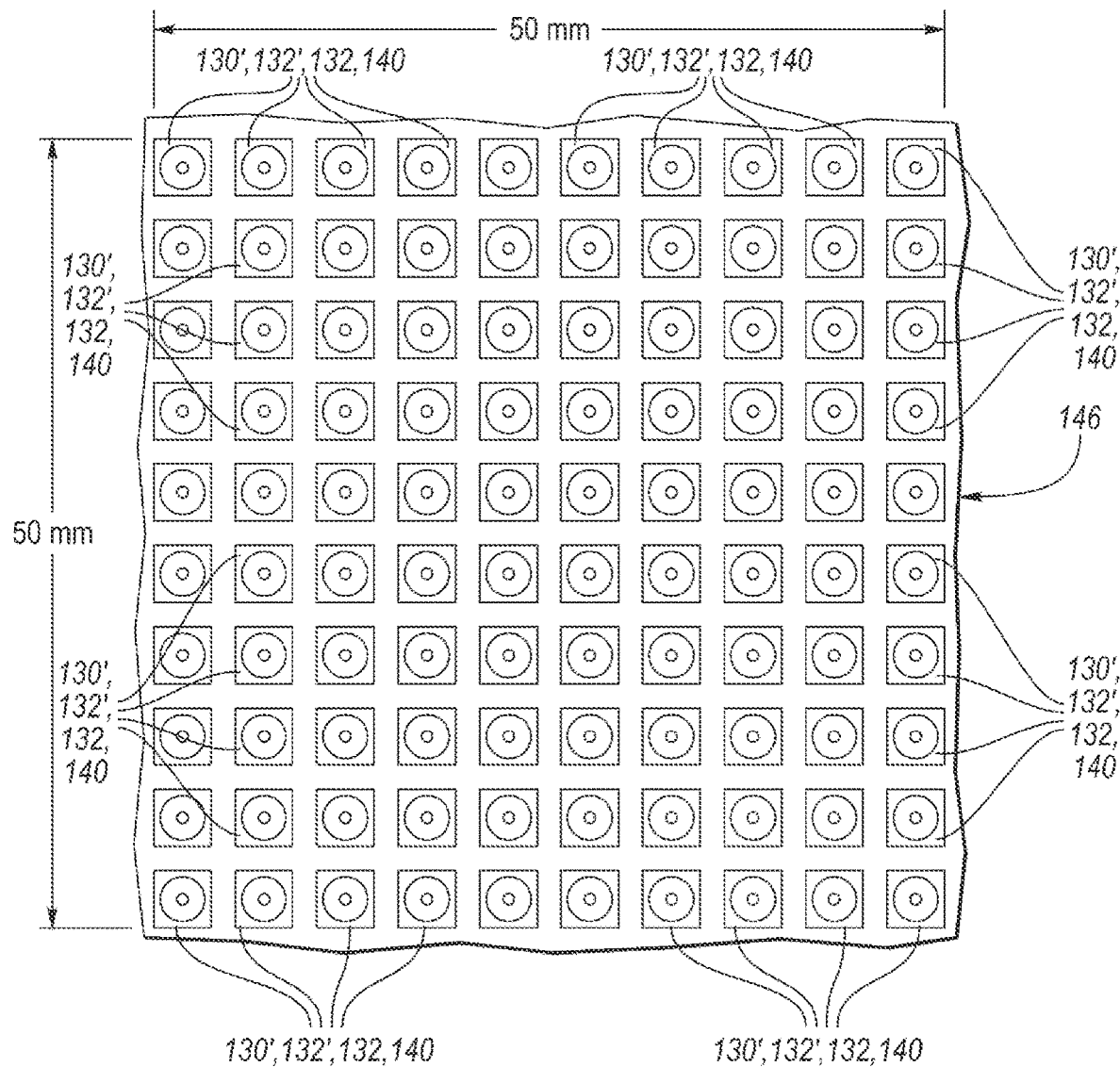
FIG. 11 is a schematic top plan view of a two dimensional, 10×10 array or sets of UV-C LEDs, visible light LEDs and/or infrared light LEDs which may populate one or more printed circuit boards; typical dimensions of the array are provided in millimeters (i.e. mm).

The layer 129' is a clear plastic surface layer 129' which comprises a UV light transmissive waveguide. One or more UV light sources 130' are optically coupled to edges of the waveguide layer 129' and are configured to emit germicidal light into the waveguide layer 129' so that the UV light travels through the waveguide layer 129' via total internal reflection (TIR) and to the outer touch surface 126' via frustrated total internal reflection (FTIF) when a user's finger is touching or is in close proximity to the outer touch surface 126' as indicated by arrow 128'. The UV light sources 130' preferably include one or more UV-C light LEDs as shown in FIG. 11.

The germicidal light is preferably UV-C light which has an intensity within a relatively narrow range of wavelengths which kills microbes without damaging healthy tissue of the customer.

Touching or near proximity to the external surface may allow for some UV light to exit the transparent film material onto the user's contact points such as fingertips and immediate surrounding areas. As a result, exiting UV light may disinfect the contacting fingertips and immediate surrounding areas including the outer, external surface of the transparent film material potentially carrying disease causing agents.

The UV light is preferably far UV-C light having a wavelength range of about 200 nm to about 230 nm.

The switch assembly 114' may further include an illumination device or visible light source 132' to illuminate at least one of the selection button 118' and the area proximate the selection button 118'. The illumination device 132' may include one or more visible light LEDs 132' as shown in the array of FIG. 11.

In summary, in the second embodiment of FIG. 7, a UV and visible light transparent film material is molded onto the layer or substrate 122' to automatically disinfect an external touch surface 126' of the film sheet 124'. UV light is emitted from the UV light source 130' into an edge of the transparent film material 129' in order to transfer the UV light through the transparent film material 129' while remaining in the transparent film material via total internal reflection (TIR). Some UV light exits the transparent film material 129' at points of contact to disinfect fingertips and immediate surrounding areas through frustrated total internal reflection (FTIR).

Each of the UV lighting devices 130' preferably comprises a far UV-C LED surface mounted device (i.e. SMD). Each device 130' may contain an integrated circuit (IC) which includes a control circuit (not shown) having a current driver and signal processing circuitry necessary to control and activate the LED function. Each control circuit may preferably include a signal shaping amplifier circuit, a constant current driver circuit and an RC oscillator.

Preferably, each UV lighting device 130' has a package size and pinouts as well as LED support locations. Each UV lighting device 130' may be supplied by Crystal IS Inc. and Asahi Kasei and, preferably, comprises an UV-C LED device 130' integrated with its IC. The devices 130' provide UV-C light in a region of the spectrum which kills microbes but does not damage healthy tissue (about 200 nm to about 230 nm). The devices 130' may be serially interconnected by signal traces on their respective PC boards such as PC board 146 in FIG. 11. Obviously, other UV-C lighting devices (even smaller than the UV-C lighting devices shown in FIG. 11) may be used if desired. If the UV-C LEDs are unable to operate in this narrow wavelength range, a filter (not shown) may be disposed between the devices 130' and the button 118' to substantially reject all UV-C light outside this narrow range.

The system also includes one or more 3-D or depth sensors such as 2.5 D volumetric or 2-D/3-D hybrid sensors, one of which is generally indicated at 110 in FIG. 9. The sensor technology is sometimes called "3-D" because it measures X, Y and Z coordinates of objects and/or humans within a scene. This can be misleading terminology. Within a given volume these sensors only obtain the X, Y and Z coordinates of the surfaces of objects; the sensors are not able to penetrate objects in order to obtain true 3-D cross-sections, such as might be obtained by a CAT scan of the human body. For this reason, the sensors are often referred to as 2½-D sensors which create 2½ dimensional surface or depth maps to distinguish them from true 3-D sensors which create 3-D tomographic representations of not just the surface, but also the interior of an object.

In spite of this distinction between 2.5-D and 3-D sensors, people in the vision industry will often speak of 2.5-D sensors as 3-D sensors. The fact that "3-D Vision" sensors create 2.5-D surface maps instead of 3-D tomographs is implicit.

Still referring to FIG. 9, preferably each sensor 110 comprises a near-infrared pattern projector or emitter 132, a pair of near-infrared cameras or detectors 134, a visible light, monochromatic or color camera 130 and a uniform light source 140 (either IR or visible light). A near infrared pattern of light is projected by the emitter 132 onto the face of the human of FIG. 9 and the reflected light is read by the one or more detectors 134 along with the information from the camera 130. In other words, the projector 132 operates in the near infrared range by means of diffractive optical elements to project several tens of thousands of laser pencils or beams onto a scene including the human face to be analyzed. The infrared cameras 134 analyze the infrared scene to locate the intersections of the laser pencils with the scene and then uses geometry to calculate the distance to the human face in the scene. The visible light camera 130 in a preferred embodiment is used to associate a color or monochrome intensity to each portion of the analyzed image.

The IR pattern emitter 132 may comprise of an infrared laser diode emitting at 830 nm and a series of diffractive optics elements (DOE). These components work together to create a laser "dot" pattern. The laser beam from the laser diode is shaped in order to give it an even circular profile then passed through two diffractive optic elements (DOE). The first element creates a dot pattern containing dots, the second element multiplies this dot pattern into a grid. When the infrared pattern is projected onto a face surface, the infrared light scattered from the surface is configured to be sensitive in the neighborhood of 830 nm.

In addition to the IR sensor or detectors 134, the camera 130 is configured to be sensitive in the visible range, with a visible light, band-pass filter operative to reject light in the neighborhood of 830 nm. During operation, the information from the IR sensors 134 is used to calculate the depth of a human face and the information from the RGB sensor 130 is used to sense the color and brightness of the human face. This provides the ability to interpret an image in what is traditionally referred to as two and a half dimensions. As previously mentioned, it is not true 3-D due to the sensor only being able to detect surfaces that are physically visible to it (i.e., it is unable to see through objects or to see surfaces on the far side of an object).

Alternatively, the 3-D or depth sensor 110 may comprise light-field, laser scan, time-of-flight or passive binocular sensors, as well as active monocular and active binocular sensors.

Preferably, the 3-D or depth sensor 110 measures distance via massively parallel triangulation using a projected pattern (a "multi-point disparity" method). The specific types of active depth sensors which are preferred are called multi-point disparity depth sensors.

"Multipoint" refers to a laser projector which projects thousands of individual beams (aka pencils) onto a scene. Each beam intersects the scene at a point.

"Disparity" refers to the method used to calculate the distance from the sensor to objects in the scene. Specifically, "disparity" refers to the way a laser beam's intersection with a scene shifts when the laser beam projector's distance from the scene changes.

"Depth" refers to the face that these sensors are able to calculate the X, Y and Z coordinates of the intersection of each laser beam from the laser beam projector with a scene.

"Passive Depth Sensors" determine the distance to humans or objects in a scene without affecting the scene in any way; they are pure receivers.

"Active Depth Sensors" determine the distance to objects or humans or human face in a scene by projecting energy onto the scene and then analyzing the interactions of the projected energy with the scene. Some active sensors project a structured light pattern onto the scene and analyze how long the light pulses take to return, and so on. Active depth sensors are both emitters and receivers.

For clarity, the sensor 110 is preferably based on active monocular, multipoint disparity technology as a "multipoint disparity" sensor herein. This terminology, though serviceable is not standard. A preferred monocular (i.e., a single infrared camera) multipoint disparity sensor is disclosed in U.S. Pat. No. 8,493,496. A binocular multipoint disparity sensor, which uses two infrared cameras 134 to determine depth information from a scene, is also preferred as shown in FIG. 9.

Multiple volumetric sensors may be placed in key locations around and above the fuel dispenser 34. Each of these sensors typically captures hundreds of thousands of individual points in space. Each of these points has both a Cartesian position in space and an associated RGB color value. Before measurement, each of these sensors is registered into a common coordinate system at the fuel dispenser 34. This gives the present system the ability to correlate a location on the image of a sensor with a real-world position. When an image is captured from each sensor, the pixel information, along with depth information, is converted by the image processor and controller/processor of FIG. 9 into a collection of points in space, called a "point cloud."

A point cloud is a collection of data representing a scene as viewed through a "vision" sensor. In three dimensions, each datum in this collection might, for example, consist of the datum in this collection might, for example, consist of the datum's X, Y and Z coordinates along with the Red, Green and Blue values for the color viewed by the sensor 110 at those coordinates. In this case, each datum in the collection would be described by six numbers. To take another example: in two dimensions, each datum in the collection might consist of the datum's X and Y coordinates along with the monotone intensity measured by the sensor 110 at those coordinates. In this case, each datum in the collection would be described by three numbers.

The controller/processor controls the cameras 134 and 130, the emitter 132 and a uniform light source 140 of the sensor 110. The uniform light source 140 preferably comprises a laser diode operating as a DOE pattern generator. The light source 140 may be configured to uniformly illuminate the surface of the target object (i.e. human face) within the scene with light having an intensity within a relatively narrow range of wavelengths such that the light overwhelms the intensity of ambient light within the narrow range to obtain reflected, backscattered illumination which is captured by one or more of the cameras 130 and 134.

The hybrid 2-D/3-D sensor 110 is used to measure color, brightness and depth at each of hundreds of thousands of pixels per sensor 110. The controller/processor together with the image processor processes the data generated by the sensor 110 in order to detect faces in the images captured. For this purpose, the controller/processor defines windows 110' at candidate locations in each image, wherein the window sizes are determined by the depth information provided by the depth cameras 134. The controller/processor applies a face detection algorithm to each such window 110' in order to determine whether the window 110' contains a human face. If so, the controller/processor applies a face recognition algorithm to identify the person to whom the face belongs. Such algorithms are well known in the art of face recognition.

The volumetric sensor 110 described above can be utilized in a method and system for deterring an unauthorized transaction at a self-service, dispensing or charging station having the previously described push button switch assembly 114. The system typically includes one or more cameras 134 and 130 configured to capture at least one image of a face of a person (i.e. FIG. 9) within a field of view of the cameras 134 and 130 at the push button switch assembly 114. The at least one image may include a depth or 3D image and each camera 134 may include a 3D image depth sensor. The assembly 114 has an outer touch surface 126 (or the outer touch surface 126' of the second embodiment) configured to be pressed by the person of FIG. 9 to initiate a dispensing or charging transaction. The system further includes a memory device configured to store data containing facial characteristics or features of known, suspicious persons. The memory device may be located at the station (as shown in the controller of FIG. 9) or remotely from the station. The processor or controller is configured to determine whether the person within the filed of view is a known, suspicious person or not by comparing the facial characteristics or features of the person within the field of view with the facial characteristics or features of known, suspicious persons. If located remotely from the station, the stored data can be downloaded from a system 30 over the communication link 28 of FIG. 1.

The IR light source or emitter 132 is configured to illuminate the face of the person of FIG. 9 with structured IR light to obtain the reflected, backscattered IR radiation wherein the cameras 134 are configured to sense the reflected, backscattered IR radiation to obtain the at least one image of the person's face.

The light source 140 may be configured to uniformly illuminate the face of the person with visible or IR light having an intensity within a relatively narrow range of wavelengths such that the light overwhelms the intensity of ambient light within the narrow range to obtain the reflected, backscattered illumination.

The controller or processor may be configured to generate a blocking or disabling signal (to fuel or charging lockout devices of FIG. 10) to prevent the initiation of a refueling or charging transaction upon determining that the person within the field of view of the cameras 130 and 134 is a known, suspicious person. In addition, or alternatively, the controller or processor may be configured to activate or alter at least one sensory indicator such as blinking or flashing light to deter the initiation of the transaction upon determining that the person within the field of view is a known, suspicious person.

Referring again to FIGS. 9 and 10, there is illustrated a system for deterring fueling of the vehicle 104 at the fueling or charging station with an improper grade or type of fuel or with an improper charging connector, respectively. The system includes a stationary communication device such as an RF transceiver at the station which is configured to receive wireless signals transmitted by a mobile communication device such as an RF transceiver mounted on the vehicle 104 when located proximate the station. The mobile communication device is typically controlled by the vehicle's electronic control unit (ECU) via a controller.

Each of the transmitted signals from the vehicle-mounted RF transceiver contains identification data which may identify proper grade or type of fuel for the vehicle or the type of vehicle to be fueled. The system includes the plurality of push button switch assemblies 114. Each of the assemblies 114 is manually operable to allow a customer (such as the human in FIG. 9) to initiate a fuel dispensing or charging transaction at the fueling or charging station, respectively.

The system also includes one or more sensory indicators, such as visible light sources 132' (i.e. FIG. 10), which are located at the station and are configured to controllably indicate proper, marginally acceptable and improper grade or fuel types for the vehicle 104 by providing a visual alert to the customer.

Figure 10:
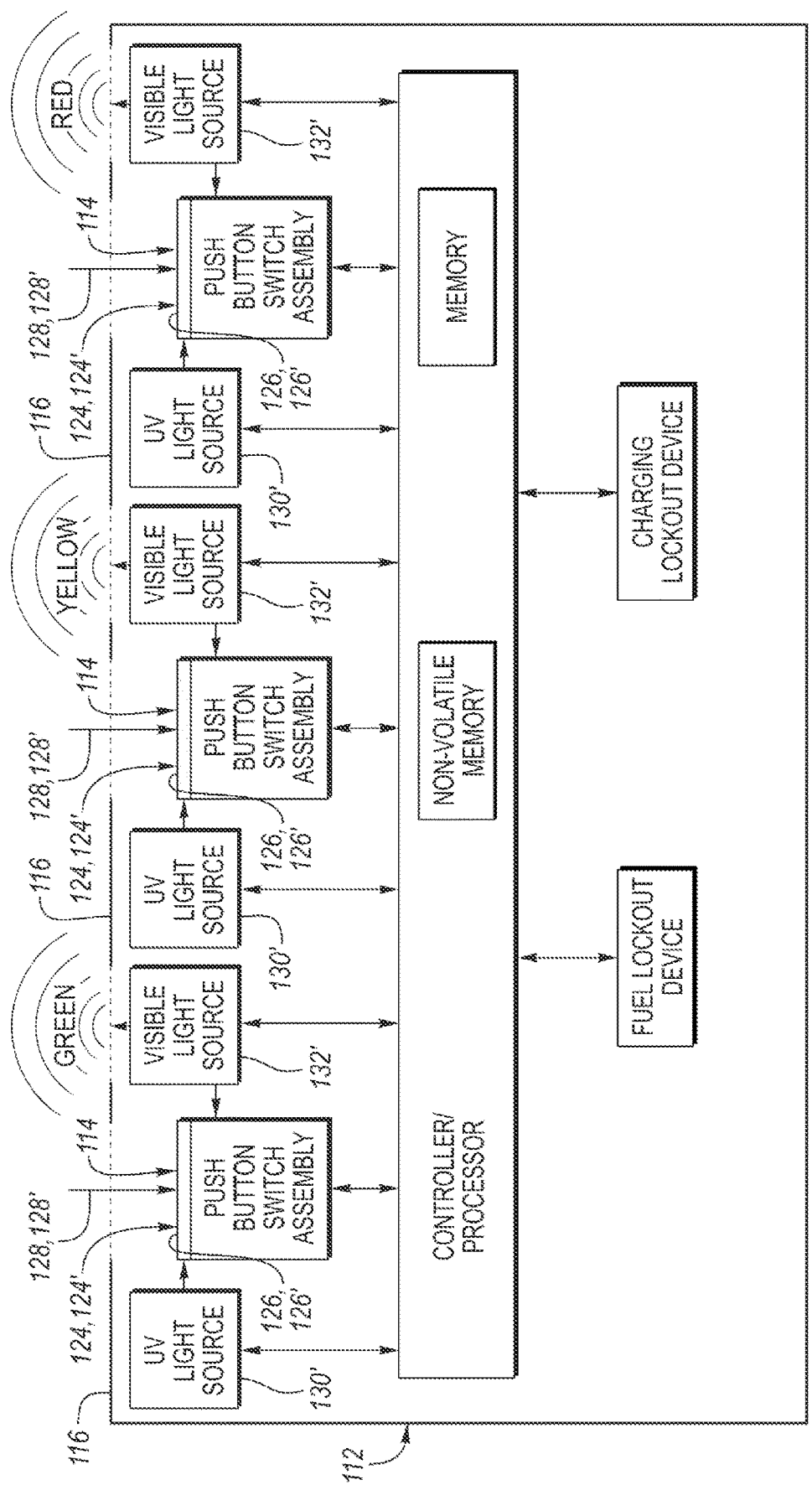
FIG. 10 is a block diagram including the apertured housing of the fuel dispenser of FIG. 9 which also includes a plurality of UV and visible light sources, push button switch assemblies and lockout devices all electrically connected or coupled to the controller/processor.

The controller/processor is coupled to the stationary communication device (i.e. the RF transceiver), the bush button assemblies 114 and the one or more sensory indicators (i.e. light sources 132') and is configured to determine the proper grade or type of fuel for the vehicle 104 by processing the identification data and to activate or alter the one or more visible light sources 132' of FIG. 10 based at least upon the determined proper grade or type of fuel to provide a visible alert to assist the customer to select the proper push button switch assembly 114 to operate the fuel dispenser 112.

The system may further include a detector or sensor coupled to the controller or processor and configured to provide a signal when a vehicle such as the vehicle 104 is physically present within a designated area at the fueling station as shown in FIG. 9. The sensor or detector may comprise one of the cameras 130 or 134 having a field of view and configured to capture at least one image of the vehicle 104 within the field of view at the fueling station.

Each indicator visible light source of FIG. 10 (such as visible light LEDs 132' of FIG. 11) typically includes individually addressable, multi-colored lighting elements and a control circuit to individually control the lighting elements based on an activation scheme so that a desired illumination is displayed. Color (i.e. green, yellow or red) and amount of light emitted by each of the lighting elements is controlled by its control circuit by controlling the intensity of light emitted by each of its lighting elements in accordance with the activation scheme. As a result, the visible light sources 132' of FIG. 10 may emit different flashing colors to indicate an improper fuel (flashing red), a proper fuel (flashing green) or a marginally acceptable fuel (a flashing yellow).

As previously mentioned, the controller or processor is also configured to generate a disabling or blocking signal to prevent the initiation of a fuel dispensing transaction with an improper grade or type of fuel via a fuel lockout device or to prevent the initiation of a fueling transaction. In like fashion, the controller can transmit a disabling or blocking signal to a charging lockout device when so desired.

The dispenser 112 may include a physical presence detector or sensor that is in communication with the processor. The physical presence detector or sensor (such as one of the cameras 130 and 134) can indicate that a human (i.e. the human of FIG. 9) or an object (such as the vehicle 114) has entered into a designated area or defined zone adjacent the charging or fueling station.

The detector/sensor may be activated by motion, sound, thermal voice or other indicia of physical presence, or any combination of the above. These can be, in particular, passive detectors that sense body heat, those that send out pulses of ultrasonic waves and measure the reflection off a moving object, microwave active sensor that send out microwave pulses and measures the changes due to reflection off a moving object similar to a police radar gun, and tomographic systems that sense disturbances to radio waves. Many existing detectors use dual-technologies, but these have to be well configured to decrease the frequency of "false positives," while increasing the detectors' efficiencies.

As previously mentioned, the physical presence detector can communicate information that a person or object (i.e. vehicle) has entered the defined zone at the station. That information will be communicated to the processor. The fueling dispenser 112 may include a mechanism to provide one or more visual indicators adjacent their respective push buttons so as to inform the customer which selector button to push. A green flashing light may indicate a proper fuel, a yellow flashing light may indicate a marginally acceptable fuel and a red flashing light may indicate an unacceptable fuel. The dispenser 112 may also include a mechanism to provide one or more acoustic indicators so as to inform the customer via unique tones of actions required to select the proper fuel or fuel type.

One form of the indicator may comprise one or more light sources 132' such as light-emitting diodes (LEDs) (as shown in FIGS. 10 and 11). The indicator is preferably a light source, such as an LED or an array of LEDs.

In one particularly preferred embodiment, the optical indicator signaling the customer is in the form of one or more flashing lights along at least one side of the enclosure adjacent the push buttons. The flashing lights may comprise or are coupled to light sources that can wholly or partially illuminate the push buttons with different colors which may flash. The light emitting assemblies may also comprise distinct light emitting objects arranged along a path adjacent the push buttons. Thus, separate LEDs may be provided to be lighted in accordance with a prescribed lighting scheme or algorithm. The lights may be pulsating, flashing or change color in order to improve visibility to signal the customer that the customer is to push a certain push button in order to properly fuel the customer's vehicle.

In one embodiment, the visual indicators may emit red, yellow and green colors or different colors, which are produced by LED lights located around the perimeter of the push buttons.

When conditions require use of one dispenser versus another dispenser for proper refueling, the controller may disable the use of the one dispenser and/or provide an alert that use of the other dispenser is required. Such disabling can be made via a mechanical device that actuates to inhibit a path in which a push button travels. For example, a controller may activate an actuator that moves a blocking or lockout device to prevent a button of the dispenser from full movement, thereby preventing the improper fuel from being dispensed. Alternatively, if a particular fuel or fuel type can be dispensed automatically due to a signal received by a proximity sensor or a push button, the controller can cause the signal that is normally sent from the sensor or push button to be blocked. This example and other examples are contemplated that can cause the disabling of a dispenser when activation of that dispenser would not result in proper fueling.

Along with or alternative to audio and visual indicators, tactile indicators (e.g., vibration indicators) can be utilized to indicate proper or improper fueling.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. An antimicrobial, push button switch assembly for use at a self-service dispensing or charging station, the assembly comprising:
a housing; and
a selection button supported for bi-directional movement within an opening in the housing and including a plastic substrate and a plastic film sheet bonded to the substrate in a molding process, the film sheet having an outer touch surface configured to be pressed by a customer to initiate a dispensing or charging transaction wherein the film sheet is configured to allow at least one of germicidal light and antimicrobial agents to travel therethrough to the outer touch surface to disinfect the outer touch surface of pathogenic microorganisms; and
wherein the film sheet includes a clear plastic surface layer which has the antimicrobial agents which exhibit controlled migration through the surface layer to the outer touch surface.

2. The assembly as claimed in claim 1, wherein the film sheet includes a clear plastic surface layer which comprises a UV light transmissive waveguide.

3. The assembly as claimed in claim 2, further comprising a UV light source optically coupled to the waveguide and configured to emit germicidal light into the waveguide so that the UV light travels through the waveguide to the outer touch surface.

4. The assembly as claimed in claim 3, wherein the switch assembly has a normally open state and a temporary closed state to electrically close a normally open control circuit or controller when the touch surface is pressed.

5. The assembly as claimed in claim 1, wherein the film sheet comprises a UV light transmissive waveguide.

6. The assembly as claimed in claim 2, further comprising a UV light source optically coupled to the film sheet and configured to emit germicidal light into the film sheet so that the UV light travels through the film sheet to the outer touch surface.

7. The assembly as claimed in claim 1, wherein the switch assembly has a normally open state and a temporary closed state to electrically close a normally open control circuit or controller when the touch surface is pressed.

8. The assembly as claimed in claim 1, wherein the molding process is an injection molding process during which plastic of the substrate is injected into a mold cavity and wherein temperature and pressure within the mold cavity is sufficient to melt a bottom surface of the film sheet during the injection molding process to bond the substrate to the film sheet and wherein the mold cavity has a shape defining the selection button.

9. The assembly as claimed in claim 1, wherein the germicidal light is UV light which has an intensity within a relatively narrow range of wavelengths which kills microbes without damaging healthy tissue of the customer.

10. The assembly as claimed in claim 9, wherein the UV light is far UV-C light having a wavelength range of about 200 nm to about 230 nm.

11. The assembly as claimed in claim 1, further comprising an illumination device to illuminate at least one of the selection button and the area proximate the selection button.

12. The assembly as claimed in claim 11, wherein the illumination device includes an array of visible light LEDs.

13. The assembly as claimed in claim 3, wherein the UV light source includes an array of UV light LEDs.

14. The assembly as claimed in claim 1, wherein the film sheet is a pre-painted film sheet which provides information to the customer.

15. The assembly as claimed in claim 1, wherein the film sheet includes a clear plastic layer which comprises an acrylic polymer clear coat layer.

16. The assembly as claimed in claim 1, wherein the plastic substrate is molded from a thermoplastic resin and has an outer surface.

17. The assembly as claimed in claim 16, wherein the plastic film sheet has a membrane bonded to the outer surface of the substrate.

18. The assembly as claimed in claim 17, wherein the plastic film sheet includes a layer of acrylic color bonded to the membrane and separate from the substrate.

19. The assembly as claimed in claim 18, wherein the plastic film sheet includes a layer of polyvinylidene fluoride overlying and protecting the layer of acrylic color.

* * * * *